United States Patent
Champleboux

(10) Patent No.: US 6,296,483 B1
(45) Date of Patent: Oct. 2, 2001

(54) SYSTEM FOR PREPARING THE PLACING OF A DENTAL IMPLANT

(75) Inventor: Guillaume Champleboux, Voiron (FR)

(73) Assignee: Universite Joseph Fourier, Grenoble (FR)

( * ) Notice: Subject to any disclaimer, the term of this patent is extended or adjusted under 35 U.S.C. 154(b) by 0 days.

(21) Appl. No.: 09/380,889

(22) PCT Filed: Mar. 3, 1997

(86) PCT No.: PCT/FR98/00412

§ 371 Date: Dec. 14, 1999

§ 102(e) Date: Dec. 14, 1999

(87) PCT Pub. No.: WO98/40030

PCT Pub. Date: Sep. 17, 1998

(30) Foreign Application Priority Data

Mar. 7, 1997 (FR) .................................................. 97 02950

(51) Int. Cl.[7] .................................................. A61C 3/00
(52) U.S. Cl. .................................................. 433/75
(58) Field of Search .......................... 433/75, 70, 71, 433/72, 74, 76

(56) References Cited

U.S. PATENT DOCUMENTS 3,919,772 * 11/1975 Lenczycki ........................ 433/173
5,015,183    5/1991 Fenwick ............................... 433/76
5,133,660 *  7/1992 Fenick ................................. 433/76
5,320,529 *  6/1994 Pompa ................................. 433/76
5,556,278 *  9/1996 Meitner .............................. 433/75
5,580,244 * 12/1996 White .................................. 433/37
5,718,579 *  2/1998 Kennedy ............................ 433/75
5,800,168 *  9/1998 Cascione et al. .................. 433/75

FOREIGN PATENT DOCUMENTS 2705027     11/1994 (FR) .
WO 94 26200 11/1994 (WO) .

* cited by examiner

*Primary Examiner*—John J. Wilson
*Assistant Examiner*—Melba Bumgarner
(74) *Attorney, Agent, or Firm*—Arthur L. Plevy; Duane Morris

(57) ABSTRACT

A system of transfer of a simulated position of a dental implant from an X-ray scanner to a robot for drilling a cradle of reproduction, in complementary shape, of a dental casting. The system includes at least one mechanical support and means adapted to removably connecting in a reproducible position the cradle to the support, the cradle containing at least two rectilinear non-concurrent elements visible by X-rays.

10 Claims, 1 Drawing Sheet

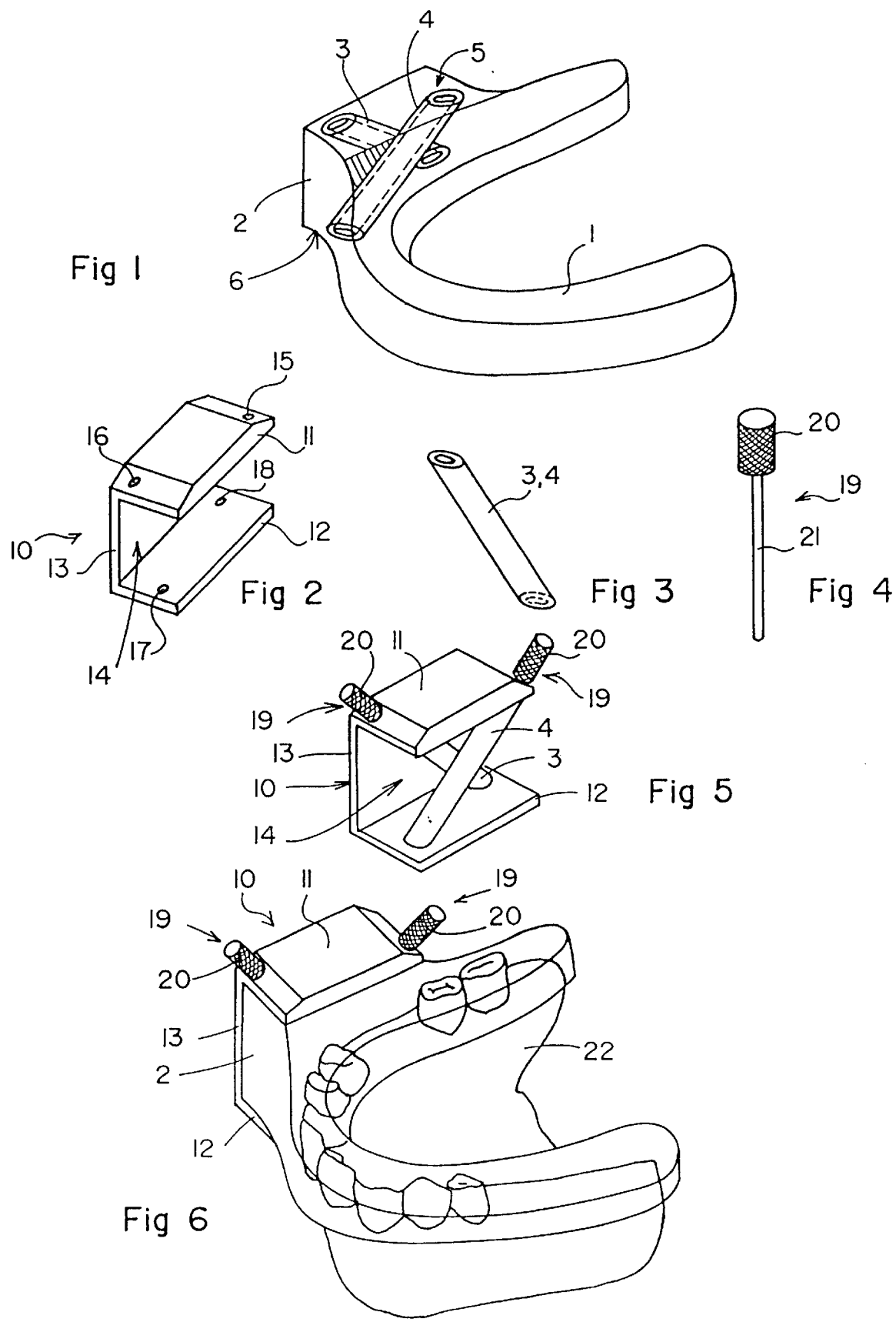

SYSTEM FOR PREPARING THE PLACING OF A DENTAL IMPLANT

BACKGROUND OF THE INVENTION

1. Field of the Invention

The present invention relates to the placing of dental implants intended for maintaining prosthesis.

2. Discussion of the Related Art

When a patient's dentition is greatly damaged, it may be envisaged to replace the missing teeth with dental prostheses. In a preferred placing method, the prostheses are anchored in the maxilla or in the mandible via one or several implants screwed in the involved jaw.

A difficulty is that, when a patient's dentition is greatly damaged, the osseous system of its jaws is also often in a poor condition. The locations where it is possible to place the implants are thus strongly limited and must be determined with great precision.

A conventional method of determining the implant position includes the following steps.

Step I

Taking a print of the jaw to be implanted by means of a printing material such as silicon, an alginate, a hydrocolloid, etc. and casting a plaster model based on this print.

Step II

Forming a transparent resin cradle, the aim of which is to bear an opaque radio mark that indicates in the mouth the location where the implant is desired to be placed in the bone. This cradle is shaped based on the plaster model. It is the negative reproduction of this model on which it must be able to intimately fit. The cradle surfaces that do not engage with the plaster model may have any shape. Based on an analysis of the teeth shape and of the patient's masticatory system, the surgeon generally determines a priori the locations where he estimates that it would be desirable to anchor the prosthesis and to place the implants.

Step III

The implant locations are materialized with are materializing cylinders or cones in a material visible by X-rays such as gutta-percha, arranged in the cradle with orientations corresponding to the estimated drilling axes. It must then be determined whether these estimated drilling axes, ideal from the prosthetic point of view, are compatible with the bone structure of the jaw.

Step IV

The patient puts the cradle in his mouth and is submitted to an X-ray scanner examination. The acquisition of the scanner cross-sections is gene rally performed in the axial plane (that is, parallel to the lower edges of the horizontal branch of the mandible). The radiologist is asked to provide cross-sections approximately crossing the desired implant position. For this purpose, the radiologist uses the opaque radio mark included in the cradle to indicate to the scanner software the desired implant location. The scanner software then calculates an image crossing this mark and perpendicular to the acquisition cross-section plane. Based on this calculated image, the dentist defines if he can put the implant in this location while respect to the different endo-osseous elements and the approximate trajectory. If he cannot put it in this location, he estimates the displacement to another position with respect to the mark included in the cradle. All these estimates are used to place, with no numerical parameters, the implant in the mouth.

Step V

The cradle is removed from the patient's mouth, after which, in some implementations, a drilling of the cradle is performed to be subsequently used as a guide for the jaw drilling at the location where the implant is desired to be inserted.

A problem that is raised in implementing such a method is due to the transfer of information relating to the optimal drilling axis obtained based on the scanner images to the drilling guide formed by the cradle. To be able to use the information provided by the scanner software and images, it is necessary to know the transformation linking the scanner imagery reference system to a reference system in which the cradle drilling is performed. It is also necessary to locate this cradle in the referential in which its drilling is performed.

It has already been provided to coat the outer surface of the cradle (step II hereabove) with a partially radio-opaque material to make this surface visible on the scanner images. Thus, the (three-dimensional) surface of the cradle can be located in the scanner referential, that is, a set of surface points can be acquired in scanner images (step IV hereabove). Once the cradle is removed from the patient's mouth, it is placed in a medium of optical or mechanical determination of a three-dimensional sensor. This sensor is used to locate the cradle surface in the drilling referential. The placing of the two surfaces (cradle surface acquired in the scanner referential and cradle surface located by the sensor) in correspondence enables one to determine the rigid transformation (transfer array) between the two referentials respectively linked to the scanner and to the sensor. The information relating to the position of the implant drilling axis, or the respective positions of the different drilling axes for different implants, can thus be transferred from the scanner images to the mechanical referential of the sensor in which a drilling robot is positioned.

Such a solution, described in French patent application NO. 2,705,027 however requires use of an optical or mechanical sensor to obtain this information transfer.

SUMMARY OF THE INVENTION

The present invention aims at providing a novel solution to transfer information relating to a drilling axis obtained in the scanner referential to a referential associated with the drilling guide, that is, with the cradle.

The present invention also aims at providing a solution that does not require use of an optical or mechanical three-dimensional sensor.

To achieve these objects, the present invention provides a cradle adapted for the placing of a dental implant including, in a protrusion of an external contour, at least two hollow rectilinear non-concurrent tubes emerging on either side of the protrusion and locatable by X-rays.

According to an embodiment of the present invention, the respective axes of the tubes inscribe in two parallel planes, perpendicular to a plane in which the cradle inscribes.

According to an embodiment of the present invention, the axes of the tubes form an angle included between 60 and 120°, preferably 90°.

The present invention also aims at a mechanical support for a cradle adapted for the placing of a dental implant, defining an open housing for receiving a protrusion of a cradle of the above type.

According to an embodiment of the present invention, this support includes at least two spaced apart plates protruding from a base, the two plates including, each, at least two openings and each opening being adapted to facing an end of a hollow tube.

According to an embodiment of the present invention, the support is associated with at least two rods adapted to being engaged, each through an opening of one of the plates into the tube facing the opening and into an opening of the other plate.

The present invention also aims at a system for transferring a simulated position of a dental implant from an X-ray scanner to a robot for drilling a cradle that has a complementary shape with respect to a dental casting, including at least one mechanical support; and means adapted for removably connecting in a reproducible position the cradle to the support, the cradle containing at least two rectilinear non-concurrent elements, visible with X-rays.

According to an embodiment of the present invention, the two rectilinear elements integrated to the cradle are part of the connection means between the cradle and the support.

According to an embodiment of the present invention, the system is adapted to implementing a dental implant positioning method including the steps of:

positioning at least two rectilinear non-concurrent elements visible with X-rays in an open housing of a first mechanical support;

forming a cradle based on a dental casting and on the mechanical support, to integrate said elements in the cradle;

placing the cradle, removed from the support, in the mouth, and performing scanner tomographic cross-sections of this cradle and of the corresponding jaw;

determining with a simulation software the optimal position of at least one implant to be performed;

determining, in a referential associated with the rectilinear elements, ideal drilling axes determined by the analysis of the scanner images;

positioning the cradle in a second support, identical to the first one and linked to a robot system;

drilling, with the robot, the cradle along said axes; and placing the cradle back into the mouth and using this cradle as a jaw drilling guide for the placing of implants.

According to an embodiment of the present invention, the first and second supports are a same support equipped with removable means of attachment to the drilling robot.

The foregoing objects, features and advantages of the present invention will be discussed in detail in the following non-limiting description of specific embodiments in connection with the accompanying drawings.

BRIEF DESCRIPTION OF THE DRAWING

FIG. 1 schematically shows in a perspective view an embodiment of a cradle for preparing the placing of a dental implant according to the present invention;

FIG. 2 shows an embodiment of a mechanical support for a cradle according to the present invention;

FIG. 3 shows an embodiment of a device of reception of removable means of connection of a cradle to a mechanical support according to the present invention;

FIG. 4 shows an embodiment of a removable device of connection of a cradle to a mechanical support according to the present invention;

FIG. 5 illustrates the respective positions of a mechanical support and of connection means, for an integration of the reception devices in a cradle according to the present invention; and FIG. 6 shows a cradle according to the present invention, associated with a mechanical support and positioned on a dental casting.

For clarity, the same elements have been designated with the same references in the different drawings.

DETAILED DESCRIPTION

A feature of the present invention is to associate a cradle, adapted to implementing a dental implant positioning method, with a removable mechanical support, and to provide removable links that maintain the respective positions of the cradle and of the mechanical support when associated.

Another feature of the present invention is that part of the connection means is integrated to the cradle and is locatable by an X-ray scanner or any other three-dimensional localization system, for example, a magnetic resonance image system.

FIG. 1 schematically shows in a perspective view an embodiment of a cradle 1 according to the present invention. This cradle is formed conventionally based on a dental casting (not shown in FIG. 1), cast in a print of a jaw to be implanted of a patient. According to the present invention, cradle 1 has a protrusion 2 towards the outside of the casting shape. Protrusion 2 integrates two hollow rectilinear tubes 3, 4, the respective axes of which are, for example, contained in two parallel planes perpendicular to a plane containing cradle 1. Tubes 3 and 4 are integrated into protrusion 2 upon manufacturing of cradle 1, as will be seen hereafter.

A feature of tubes 3 and 4 is that they are made of a material visible by X-rays, to be locatable by a scanner. The axes of tubes 3 and 4 are not parallel and form, for example, an angle between 60 and 120°, preferably 90°. Tubes 3 and 4 emerge on either side of substantially planar surfaces 5, 6 of protrusion 2. Surfaces 5 and 6 are, preferably, parallel to the plane in which cradle 1 inscribes.

Tubes 3 and 4 have a double function. On the one hand, they define two non-concurrent straight lines in images reconstituted from scanner tomographic cross-sections. On the other hand, they form devices of reception of removable means of connection of cradle 1 to a mechanical support.

FIG. 2 shows an embodiment of a mechanical support according to the present invention.

According to this embodiment, support 10 has the general shape of a rigid stirrup, formed of two plates 11, 12 protruding from a base 13. Plates 11 and 12 are spaced apart and define, with base 13, a housing 14 for receiving protrusion 2 of a cradle 1 such as shown in FIG. 1.

Although it is not necessary, plates 11 and 12 are, preferably, parallel to each other, and perpendicular to base 13.

Each plate 11, 12, includes, according to the embodiment shown, four openings, respectively 15, 16, and 17, 18. These openings are aligned along the axis of a tube 3, 4 (FIG. 3) when tubes 3 and 4 are placed between plates 11 and 12 through the openings thereof.

Tubes 3 and 4 are intended for being removably connected to support 10 by means of rigid rods 19 (FIG. 4) adapted to being engaged into the openings of support 10 and into tubes 3 and 4. At least two openings, for example, openings 15, 16 of plate 11, are through holes to enable introduction of rods 19. Openings 17, 18 of the other plate 12 are not necessarily through holes but may be blind holes, that open toward plate 11.

Rods 19 have a greater length than tubes 3, 4 in addition to the thickness of plate 11 and the depth of openings 17, 18 of plate 12, to enable them to be grasped when they are in an engaged position. A grasping portion 20 of rods 19 has, for example, a greater diameter than the diameter of a connection portion 21, to form both a grasping means of these rods and a stop to the penetration of portions 21 if the four openings of support 10 are through openings.

The smaller diameter of tubes 3 and 4 is substantially equal to the outer diameter of portions 21 of rods 19, plus or minus mechanical tolerances, to avoid a clearance between support 10 and cradle 1 when the two elements are associated.

FIG. 5 illustrates the association of support 10 shown in FIG. 2 with two tubes 3 and 4 maintained between plates 11 and 12 by means of rods 19.

It should be noted that tubes 3 and 4 are not necessarily contained in two parallel planes, provided that their respective axes are not concurrent. However, an embodiment such as shown in the drawings forms a preferred arrangement of tubes 3 and 4 since it minimizes the bulk of protrusion 2 at the periphery of cradle 1 which must be adapted for being placing in a patient's mouth.

An embodiment of the present invention for preparing the placing of a dental implant will be described hereafter.

The present invention follows steps I and II of the prior method described hereabove. However, at step II, the cradle is shaped from the plaster model of the patient's teeth and the support 10 according to the present invention, such as shown in FIG. 5.

FIG. 6 illustrates the forming of a cradle 1 according to the present invention. A hardenable material, for example, a resin, is cast, not only on plaster dental casting 22 reproducing the patient's teeth, but also into the housing 14 (FIG. 5) defined by support 10, to form protrusion 2 in which tubes 3 and 4 are integrated.

Thus, the shape of protrusion 2 is perfectly adapted to the shape of housing 14 of support 10.

It should be noted that, according to the present invention, the material forming the cradle may be any material provided that it enables a scanner to locate of tubes 3, 4 present in protrusion 2.

Once the resin has hardened, rods 19 are removed to separate support 10 of protrusion 2 from cradle 1 and a cradle such as shown in FIG. 1 is obtained.

An X-ray scanner examination of the cradle placed in the patient's mouth is then performed. This examination enables reconstructing, on the images resulting from the scanner tomographic cross-sections, two straight lines corresponding to the axes of tubes 3 and 4, from which a three-dimensional reference system is deduced.

The surgeon then determines, by means of the scanner images, the ideal drilling axis for the placing of a dental implant. This drilling axis is determined in the scanner reference system, and thus also in the referential associated with tubes 3 and 4.

An advantage of the present invention is that, due to tubes 3, 4, integrated therein, cradle 1 can be repositioned in support 10, while respecting its original position by means of two rods 19. The use of two rods prevents any motion of the cradle with respect to the support. Thus, cradle 1 can be connected, via support 10, to a drilling robot, the referential of which can be the same as that associated with tubes 3, 4. Indeed, the position of tubes 3, 4 is invariant with respect to support 10 when the cradle is associated with the support. The robot can thus be driven so that its drilling axis exactly coincides with the position of the axis defined by the analysis of the scanner images and the drilling is performed in cradle 1 exactly at the desired location and according to the desired direction. This operation is of course repeated if several implants are envisaged.

The dental surgeon will then have to place the cradle back into the patient's mouth and to drill through the jaw by guiding his drill on the hole formed in cradle 1.

As an alternative, a third plate (not shown) may close one side of housing 14, to ease the subsequent repositioning of cradle 1 in support 10. Housing 14 then remains open in two non-parallel directions to enable the extraction and the introduction of extension 2 of cradle 1.

It should be noted that the support associated with the drilling robot is not necessarily the same as the support used to form cradle 1. Indeed, it may according to the present invention be provided to use several identical supports, that is, in which the positions of plates 11, 12 with respect to each other and in which the positions of openings 15, 16, 17, 18 are identical, so that a same cradle may be associated with different supports. This enables, in particular, that a support be permanently attached to the drilling robot. Similarly, this enables using cradle casting tools equipped with an unremovable support 10.

It should also be noted that the only single-use components are tubes 3, 4 to be integrated to cradle 1, support 10 and rods 19 being reusable.

Thus, an essential aspect of the present invention is the association of rectilinear elements locatable by a scanner with a removable mechanical support enabling maintaining, without using other measurements, a same reference system in the scanner referential and in a mechanical referential.

Of course, the present invention is likely to have various alterations, modifications and improvements which will readily occur to those skilled in the art. In particular, different materials (metal, ceramic) may be chosen to make support 10 and rods 19, these materials having to be as wear-resistant as possible. Indeed, the introduction of rods 19 into the support openings is a source of wearing to be avoided. Thus, for example, a ceramic or stainless steel will be preferred to aluminum. Tubes 3, 4 will be chosen to be made of a material that generates no artifacts during the scanner analysis, that has a sufficiently contrasted scanner track with respect to the tissue and bones and that has a sufficient resistance. Titanium or aluminum will for example be chosen. Further, although two tubes advantageously suffice to implement the present invention, it may be provided to associate more than two tubes with a support adapted for this purpose. Further, other three-dimensional localization systems than an X-ray scanner may be used.

What is claimed is:

1. A cradle (1) adapted for assisting in the placement of a dental implant comprising; a cradle with an external contour; a lateral protrusion (2) extending from said external contour of said cradle; at least two hollow rectilinear non-concurrent tubes (3, 4) disposed in said lateral protrusion (2), said at least two tubes emerging from at least one side of the protrusion and locatable by X-rays.

2. The cradle of claim 1, wherein the respective axes of the tubes (3, 4) are inscribed in two parallel planes, and said two parallel planes are perpendicular to a plane in which the cradle (1) is inscribed.

3. The cradle of claim 1, wherein the axis of one of said at least two tubes (3, 4) emerging from at least one side of said protrusion forms an angle between 60 and 120°, with respect to the axis of the second of said at least two tubes emerging from said protrusion.

4. The cradle of claim 1, wherein the axes axis of one of said at least two tubes (3, 4) emerging from at least one side of said protrusion forms a 90° angle with respect to the axis of the second of said at least two tubes emerging from said protrusion.

5. A mechanical support (10) for a cradle (1) adapted for assisting in the placement of a dental implant, said support comprising:

an open housing (14) for receiving a lateral protrusion (2) extending from an external contour of the cradle, said housing including openings (15, 16; 17, 18) adapted for receiving the ends of at least two hollow rectilinear non-concurrent tubes (3, 4) of cradle, wherein the respective axes of the openings of the support define at least two rectilinear non-concurrent lines.

6. The support of claim 5, further comprising at least two spaced apart plates (11, 12) protruding from a base (13), each plate including at least two of said openings (15, 16; 17, 18).

7. The support of claim 6, further comprising at least two rods (19), each of said rods adapted for engagement through an opening (15, 16) of one plate (11) and into an opening (17, 18) of the other plate (12).

8. A system for transferring a simulated position of a dental implant from an X-ray scanner to a robot for drilling a cradle (1) produced in a complementary shape of a dental casting (22), including:

at least one mechanical support (10) comprising an open housing (14) for receiving a lateral protrusion extending from an external contour of the cradle; said support including openings (15, 16; 17, 18), adapted for receiving the ends of at least two hollow rectilinear non-concurrent tubes (3, 4) locatable by X-rays, at least two tubes emerging from at least one side of said lateral protrusion wherein the respective axes of the openings of the support define at least two rectilinear non-concurrent lines; and means (3, 4, 19) adapted for removably connecting the cradle (1) to the support (10) in a reproducible position.

9. A method for dental implant positioning comprising the steps of:

positioning at least two rectilinear non-concurrent elements (3, 4) visible with X-rays in an open housing (14) of a first mechanical support (10);

forming a cradle (1) based on a dental casting (22) and on the mechanical support (10), to integrate said elements (3, 4) in the cradle (1);

placing the cradle (1), removed from the support (10), in a mouth, and performing scanner tomographic cross-sections of the cradle and of the corresponding jaw;

determining with a simulation software the optimal position of at least one implant to be performed;

determining in a referential associated with the rectilinear elements (3, 4), ideal drilling axes by the analysis of the scanner images;

positioning the cradle (1) in a second support (10), identical to the first support and linked to a robot system;

drilling the cradle (1) along said axes with the drilling robot of the robot system; and placing the cradle (1) back into the mouth and using the cradle as a jaw drilling guide for the placing of implants.

10. The method of claim 9, wherein the first and second supports are equipped with removable means of attachment to the drilling robot.

* * * * *